US007183385B2

(12) United States Patent
Comb et al.

(10) Patent No.: US 7,183,385 B2
(45) Date of Patent: Feb. 27, 2007

(54) PHOSPHO-SPECIFIC ANTIBODIES TO FLT3 AND USES THEREOF (75) Inventors: Michael J. Comb, Manchester, MA (US); Randall K. Wetzel, Stoneham, MA (US); Jiong Wu, Salem, MA (US); Katherine Crosby, Middleton, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 430 days.

(21) Appl. No.: 10/368,912

(22) Filed: Feb. 18, 2003

(65) Prior Publication Data

US 2003/0219827 A1    Nov. 27, 2003

Related U.S. Application Data (60) Provisional application No. 60/358,153, filed on Feb. 20, 2002.

(51) Int. Cl.
    C07K 16/00    (2006.01)
    C12P 21/08    (2006.01)
    G01N 33/53    (2006.01)
(52) U.S. Cl. .............................. 530/387.1; 530/388.1; 530/387.7; 530/389.1; 435/7.1
(58) Field of Classification Search ............. 530/387.1, 530/388.1, 387.7; 435/7.1
    See application file for complete search history.

(56) References Cited

U.S. PATENT DOCUMENTS 5,635,388 A    6/1997    Bennett et al.
5,777,084 A    7/1998    Buhring
6,156,882 A    12/2000   Buhring

OTHER PUBLICATIONS

PharMingen (Transduction Laboratories and PharMingen 1999 Cell Biology Sourcebook, 1999, pp. 242-245).*
Glenney et al (Journal of Immunological Methods, 1988, 109:277-285).*
Aaronson, *Science 254*: 1146-52 (1991).
Schlessinger et al., *Neuron 9*: 383-391 (1992).
Neāl et al., *Lancet 1*: 366-68 (1985).
Sainsbury et al., *Lancet 1*: 1398-1402 (1987).
Yokota et al., *Lancet 1*: 765-67 (1986).
Fukushige et al., *Mol. Cell. Biol. 6*: 955-58 (1986).
Rosnet et al., *Blood 82*(4): 1110-1119 (1993).
Casteran et al., *Cell Mol. Biol. 40*(3): 443-56 (1994).
Beslu et al., *J. Biol. Chem. 271*: 20075-81 (1996).
Whitman et al., *Cancer Res. 61*(19): 7233-39 (2001).
Kottardis et al., *Blood 98*(6): 1752-59 (2001).
Timeus et al., *Lab Invest. 81*(7): 1025-37 (2001).
Zwierzina et al., *Leukemia 13*(4): 553-57 (1999).
Abu-Duhier et al., *Br. J. Haematol 113*(4): 983-88 (2001).
Naoe et al., *Cancer Chemother. Pharmacol. 48*: Suppl. 1: S27-30 (2001).
Weisberg et al., *Cancer Cell 1*(5): 433-43 (2002).
Kelly et al., *Cancer Cell 1*(5): 421-32 (2002).
Wybenga-Groot et al., *Cell 106*(6): 745-57 (2001).

* cited by examiner

*Primary Examiner*—Jeffrey Siew
*Assistant Examiner*—Sean E Aeder
(74) *Attorney, Agent, or Firm*—Cell Signaling Technology Inc.; James G. Cullem, Esq.; Andrew J. Warner, Esq.

(57) ABSTRACT

The invention discloses two newly-discovered Flt3 phosphorylation sites, tyrosine 589 (Tyr589) and tyrosine 591 (Tyr591) in the intracellular domain, and provides antibodies, both polyclonal and monoclonal, that selectively bind to Flt3 when phosphorylated at these novel sites. Also provided are assays utilizing these reagents, including methods for determining the phosphorylation of Flt3 in a biological sample, selecting a patient suitable for Flt3 inhibitor therapy, profiling Flt3 activation in a test tissue, and identifying a compound that modulates phosphorylation of Flt3 in a test tissue, by using a detectable reagent, such as the disclosed antibodies, that binds to Flt3 when phosphorylated at Tyr589 or Tyr591. The sample or test tissue may be taken from a subject suspected of having cancer, such as acute myelogenous leukemia (AML).

15 Claims, 5 Drawing Sheets

Figure 1: Flt-3 Amino Acid Sequence

```
  1 mpalardggq lpllvvfsam ifgtitnqdl pvikcvlinh knndssvgks ssypmvsesp
 61 edlgcalrpq ssgtvyeraa vevdvsasit lqvlvdapgn isclwvfkhs slncqphfdl
121 qnrgvvsmvi lkmtetqage yllfiqseat nytilftvsi rntllytlrr pyfrkmenqd
181 alvcisesvp epivewvlcd sqgesckees pavvkkeekv lhelfgmdir ccarnelgre
241 ctrlftidln qtpqttlpql flkvgeplwi rckavhvnhg fgltwelenk aleegnyfem
301 stystnrtmi rilfafvssv arndtgyytc ssskhpsqsa lvtivekgfi natnssedye
361 idqyeefcfs vrfkaypqir ctwtfsrksf pceqkgldng ysiskfcnhk hqpgeyifha
421 enddaqftkm ftlnirrkpq vlaeasasqa scfsdgyplp swtwkkcsdk spncteeite
481 gvwnrkanrk vfgqwvssst lnmseaikgf lvkccaynsl gtscetilln spgpfpfiqd
541 nisfyatigv cllfivvltl lichkykkqf ryesqlqmvq vtgssdneyf yvdfreyeyd
601 lkwefprenl efgkvlgsga fgkvmnatay gisktgvsiq vavkmlkeka dsserealms
661 elkmmtqlgs henivnllga ctlsgpiyli feyccygdll nylrskrekf hrtwteifke
721 hnfsfyptfq shpnssmpgs revqihpdsd qisglhgnsf hsedeieyen qkrleeeedl
781 nvltfedllc fayqvakgme flefkscvhr dlaarnvlvt hgkvvkicdf glardimsds
841 nyvvrgnarl pvkwmapesl fegiytiksd vwsygillwe ifslgvnpyp gipvdanfyk
901 liqngfkmdq pfyateeiyi imqscwafds rkrpsfpnlt sflgcqlada eeamyqnvdg
961 rvsecphtyq nrrpfsremd lgllspqaqv eds
```

Western blots using phospho-Flt3(Tyr591) polyclonal antibody.

FIGURE 4

Western Blot of extracts using a total Flt3 antibody (lanes 1 and 2) or a phospho-Flt3(Tyr591) monoclonal antibody (lanes 3 and 4).

FIGURE 5

Flow cytometry using phospho-Flt3 (Tyr591) polyclonal antibody on extracts of stimulated (blue peak) or unstimulated (red peak) with the Flt3 ligand.

FIGURE 6

Flow cytometry using phospho-Flt3 (Tyr591) monoclonal antibody on extracts of untreated (blue peak) or treated (green peaks) with a Flt3 inhibitor.

PHOSPHO-SPECIFIC ANTIBODIES TO FLT3 AND USES THEREOF

RELATED APPLICATIONS

This application claims priority to U.S. Ser. No. 60/358,153, filed Feb. 20, 2002, now abandoned.

FIELD OF THE INVENTION

The invention relates generally to antibodies, and more particularly to activation state-specific antibodies to receptor tyrosine kinases and their uses.

BACKGROUND OF THE INVENTION

Many cancers are characterized by disruptions in cellular signaling pathways that lead to uncontrolled growth and proliferation of cancerous cells. Receptor tyrosine kinases (RTKs) play a pivotal role in these signaling pathways, transmitting extracellular molecular signals into the cytoplasm and/or nucleus of a cell. Cells of virtually all tissue types express transmembrane receptor molecules with intrinsic tyrosine kinase activity through which various growth and differentiation factors mediate a range of biological effects (reviewed in Aaronson, *Science* 254: 1146–52 (1991)). RTKs share a similar architecture, having an intracellular catalytic domain, a hydrophobic transmembrane domain, and an extracellular ligand-binding domain. The binding of ligand to the extracellular portion is believed to promote dimerization, resulting in trans-phosphorylation and activation of the intracellular tyrosine kinase domain (see Schlessinger et al., *Neuron* 9:383–391 (1992)).

Biological relationships between various human malignancies and disruptions in growth factor-RTK signal pathways are known to exist. For example, overexpression of EGFR-family receptors is frequently observed in a variety of aggressive human epithelial carcinomas, such as those of the breast, bladder, lung and stomach (see, e.g., Neal et al., *Lancet* 1: 366–68 (1985); Sainsbury et al., *Lancet* 1: 1398–1402 (1987)). Similarly, overexpression of HER2 has also been correlated with other human carcinomas, including carcinoma of the stomach, endometrium, salivary gland, bladder, and lung (see, e.g. Yokota et al., *Lancet* 1: 765–67 (1986); Fukushigi et al., *Mol. Cell. Biol.* 6: 955–58 (1986)). Phosphorylation of such RTKs activates their cytoplasmic domain kinase function, which in turns activates downstream signaling molecules. RTKs are often phosphorylated at multiple different sites, such as distinct tyrosine residues. These enzymes are gaining popularity as potential drug targets for the treatment of cancer. For example, Iressa™, an inhibitor of EGFR, has recently entered clinical trials for the treatment of breast cancer.

FMS-related tyrosine kinase 3 (Flt3) is a receptor tyrosine kinase preferentially expressed in hematopoietic progenitor cells. The sequence for the human Flt3 gene has been published (see Small et al., *Blood* 15(4): 1110–9 (1993)). It has previously been shown that Flt3 is phosphorylated at tyrosine 958 in the C terminal domain (see Casteran et al., *Cell Mol. Biol.* 40(3): 443–56 (1994); Beslu et al., *J. Biol. Chem.* 271: 20075–81 (1996)). Recent studies have indicated that the Flt3 gene is mutated by internal tandem duplication in 20–25% of adults with acute myelogenous leukemia (AML), leading to phosphorylation and overactivation of Flt3 activity in cancerous cells (see Whitman et al., *Cancer Res.* 61(19): 7233–39 (2001) Kottardis et al., *Blood* 98(6): 1752–59 (2001)). AML is the most common type of leukemia in adults, with an estimated 10,000 new cases annually (source: The Leukemia & Lymphoma Society (2001)). Flt3 has also been implicated in neural-crest derived tumors and myelodysplastic syndromes (see Timeus et al., *Lab Invest.* 81(7): 1025–37 (2001); Zwierzina et al., *Leukemia* 13(4): 553–57 (1999)). Mutation of Flt3 at aspartic acid 835 (asp835) has been implicated in progression of AML (see Abu-Duhier et al., *Br. J. Haematol.* 113(4): 983–88 (2001)). Although patient risk of AML may be clinically detected by examining genetic mutation of the Flt3 gene, many diagnoses are not made until patients present with symptoms of the disease, such as easy bruising, anemia and fatigue, or low white cell count. In addition, activation of the Flt3 receptor kinase leading to AML may occur in the absence of genetic mutations of the Flt3 gene.

Inhibitors of Flt3 are presently being studied as potential AML therapeutics (see Naoe et al., *Cancer Chemother. Pharmacol.* 48: Suppl. 1: S27–30 (2001)). For example, agonist antibodies that bind the extracellular domain of Flt3 and activate its tyrosine kinase activity have been described (see U.S. Pat. No. 5,635,388, Bennett et al.). More recent results indicate that Flt3 inhibitors have anti-tumor activity in pre-clinical models (Weisberg et al., *Cancer Cell* 1(5): 433–43 (2002); Kelly et al., *Cancer Cell* 1(5): 421–32 (2002)). However, Flt3 expression alone does not always correlate with patient response (personal communication, Dr. Donald Small, Johns Hopkins University).

Accordingly, new and improved reagents for the detection of Flt3 activity would be desirable, including development of reagents against newly-identified sites of Flt3 phosphorylation. Since phosphorylation-dependent over-activation of Flt3 is associated with diseases such as AML, reagents enabling the specific detection of Flt3 activation would be useful tools for research and clinical applications.

SUMMARY OF THE INVENTION

The invention discloses two novel Flt3 phosphorylation sites, tyrosine 589 (Tyr589) and tyrosine 591 (Tyr591) in the intracellular domain, and provides antibodies, both polyclonal and monoclonal, that selectively bind to Flt3 when phosphorylated at these novel sites. Also provided are methods of determining the phosphorylation of Flt3 in a biological sample, identifying a patient suitable for Flt3 inhibitor therapy, profiling Flt3 activation in a test tissue, and identifying a compound that modulates phosphorylation of Flt3 in a test tissue, by using a detectable reagent, such as the disclosed antibodies, that binds to Flt3 when phosphorylated at Tyr589 or Tyr591. In preferred embodiments, the sample or test tissue is taken from a subject suspected of having cancer, such as AML, characterized by or involving Flt3 activity.

BRIEF DESCRIPTION OF THE DRAWINGS

This patent or application file contains at least one drawing executed in color. Copies of this patent or patent application publication with color drawing(s) will be provided by the United States Patent Office upon request and payment of the necessary fee.

FIG. 4—is a Western blot using phospho-Flt3(Tyr591) monoclonal antibody CST #25-54 on extracts of Baf3 cells transfected with Flt-3, and stimulated with Flt3 ligand. Lane 1 and 3 are cell lysate without Flt3 ligand stimulation. Lane 2 and 4 are cell lysate with Flt3 ligand stimulation. Lane 1 and 2 show Flt3 expression detected by a control antibody that is not phospho-specific. Lane 3 and 4 show phospho-Flt3 detection by phospho-Flt3(Tyr591) monoclonal antibody. Note presence of 1 band detected by phospho-Flt3 antibody in lane 4 corresponding to the expected molecular weight of 155 kDa of Flt3, demonstrating the phospho-specificity of the monoclonal antibody CST #25-54. Single band detected by the phospho-Flt3 antibody corresponds to the upper band detected by control antibody. Control antibody also detected 133 kDa form of Flt3.

DETAILED DESCRIPTION OF THE INVENTION

Figure 1:
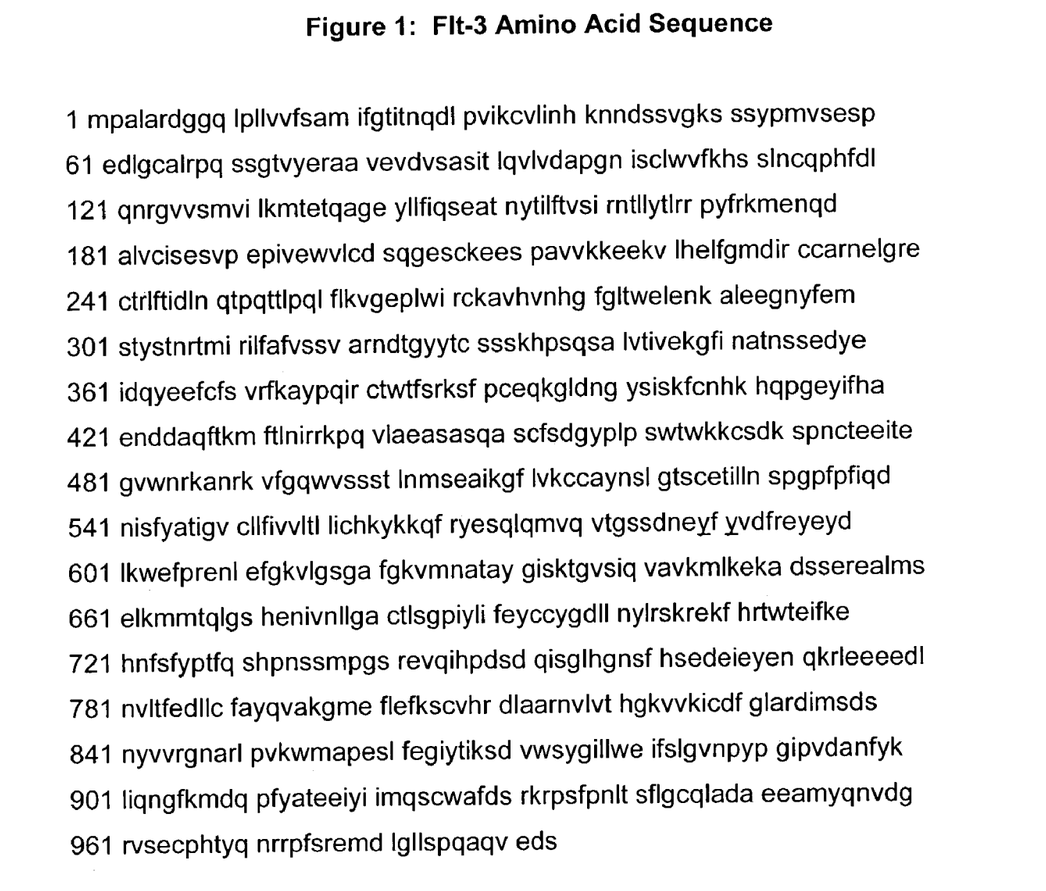
FIG. 1—is the amino acid sequence (1-letter code) of human Flt3 (SEQ ID NO: 1). Tyr589 and Tyr591 are underlined; the intracellular domain comprises residues 564 to 993.

In accordance with the present invention, two novel sites of Flt3 phosphorylation in the intracellular domain have now been identified, tyrosine 589 (Tyr589) and tyrosine 591 (Tyr591) (see FIG. 1). Although Flt3 phosphorylation at tyrosine 958 in the C-terminal domain has previously been described (see Beslu et al., supra.), the tyrosine phosphorylation sites disclosed herein have not previously been published or described. The newly identified phosphorylation sites disclosed herein were discovered by comparing the amino acid sequence of the human Flt-3 juxta-transmembrane domain with the juxta-transmembrane domain of several members of the Eph family of RTKs. Auto-phosphorylation of the Eph juxta-transmembrane domain of Eph (the roughly 30 amino acids immediately intracellular to (i.e. C-terminus to) the Eph transmembrane domain) at conserved tyrosines has been shown to regulate catalytic activity of EphB2. See Wybenga-Groot et al., *Cell* 106(6). 745–57 (2001). Phosphorylation in this domain is believed to induce a conformational change distorts the Eph kinase domain, thereby blocking formation of the proper catalytic structure. Id. Comparison of the homologous region of Flt-3 to the Eph family juxta-transmembrane domain indicated potential tyrosine phosphorylation sites at Tyr589 and Tyr591 of Flt-3. Analysis of this region of Flt-3 using the ScanSite program (scansite.mit.edu) (see also Yaffe et al., *Nat Biotechnol.* 19(4): 348–53 (2001)) confirmed Tyr589 and Tyr591 as likely sites of phosphorylation by kinases such as EGF kinase and PDGF kinase. As a result of this discovery, peptide antigens may now be designed to raise phospho-specific antibodies that bind Flt-3 when phosphorylated at Tyr589 and/or Tyr591. These new reagents enable previously unavailable assays for the detection of Flt3 phosphorylation at these sites.

The invention provides, in part, phospho-specific antibodies that bind to Flt3 only when phosphorylated at tyrosine 589 or 591. Also provided are methods of using a detectable reagent that binds to phosphorylated Flt3(Tyr589) and/or Flt3(Tyr591) to detect Flt3 phosphorylation and activation in a biological sample or test tissue suspected of containing phosphorylated Flt3 or having altered Flt3 activity, as further described below. In preferred embodiments, the detectable reagent is at least one Flt3 antibody of the invention. All references cited herein are hereby incorporated herein by reference.

A. Antibodies and Cell Lines

Flt3 phosphospecific antibodies of the present invention bind to Flt3 only when phosphorylated at Tyr589 or Tyr591, respectively, but do not substantially bind to Flt3 when not phosphorylated at either of these respective residues, nor to Flt3 when phosphorylated at other tyrosine residues. The Flt3 antibodies of the invention include (a) monoclonal antibody CST #25-54, which binds phospho-Flt3 (Tyr591), (b) polyclonal antibodies which bind to phospho-Flt3 (Tyr589) and phospho-Flt3(Tyr591), (c) antibodies (monoclonal or polyclonal) which specifically bind to the phospho-antigen (or more preferably the epitope) bound by the exemplary Flt3(Tyr589) and Flt3(Tyr591) antibodies disclosed in the Examples herein, and (d) fragments of (a), (b), or (c) above which bind to the antigen (or more preferably the epitope) bound by the exemplary antibodies disclosed herein. Such antibodies and antibody fragments may be produced by a variety of techniques well known in the art, as discussed below. Antibodies that bind to the phosphorylated epitope (i.e., the specific binding site) bound by the exemplary Flt3(Tyr589) or Flt3(Tyr591) antibodies of the Examples herein can be identified in accordance with known techniques, such as their ability to compete with labeled Flt3 antibodies in a competitive binding assay.

The preferred epitopic site of the Flt3(Tyr589) antibodies of the invention is a peptide fragment consisting essentially of about 11 to 17 amino acids including the phosphorylated tyrosine 589, wherein about 5 to 8 amino acids are positioned on each side of the tyrosine phosphorylation site (for example, residues 580–594 of SEQ ID NO: 1). The preferred epitopic site of the Flt3(Tyr591) antibodies of the invention is a peptide fragment consisting essentially of about 11 to 17 amino acids including the phosphorylated tyrosine 591, wherein about 5 to 8 amino acids are positioned on each side of the tyrosine phosphorylation site (for example, residues 584–597 of SEQ ID NO: 1).

The invention is not limited to Flt3 antibodies, but includes equivalent molecules, such as protein binding domains or nucleic acid aptamers, which bind, in a phospho-specific manner, to essentially the same phosphorylated epitope to which the Flt3 antibodies of the invention bind. See, e.g., Neuberger et al., Nature 312: 604 (1984). Such equivalent non-antibody reagents may be suitably employed in the methods of the invention further described below.

The term "antibody" or "antibodies" as used herein refers to all types of immunoglobulins, including IgG, IgM, IgA, IgD, and IgE, including $F_{ab}$ or antigen-recognition fragments thereof. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403–11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.)

The term "Flt3 antibodies" means antibodies that bind phospho-Flt3(Tyr589) and phospho-Flt3(Tyr591), both monoclonal and polyclonal, as disclosed herein. The term "does not bind" with respect to such antibodies means does not substantially react with as compared to binding to phospho-Flt3.

The term "detectable reagent" means a molecule, including an antibody, peptide fragment, binding protein domain, etc., the binding of which to a desired target is detectable or traceable. Suitable means of detection are described below.

Polyclonal antibodies of the invention may be produced according to standard techniques by immunizing a suitable animal (e.g., rabbit, goat, etc.) with an antigen encompassing pTyr(589) or pTyr(591), respectively (such as the antigen to which monoclonal antibody CST #25-54 binds), collecting immune serum from the animal, and separating the polyclonal antibodies from the immune serum, in accordance with known procedures. In a preferred embodiment, the antigen is a phospho-peptide antigen comprising the Flt3 sequence surrounding and including phospho-Tyr589 or Tyr591, respectively, the antigen being selected and constructed in accordance with well known techniques. See, e.g., ANTIBODIES: A LABORATORY MANUAL, Chapter 5, p. 75–76, Harlow & Lane Eds., Cold Spring Harbor Laboratory (1988); Czernik, *Methods In Enzymology*, 201: 264–283 (1991); Merrifield, *J. Am. Chem. Soc.* 85: 21–49 (1962)). Particularly preferred peptide antigens, CSDNEY*FYVDF (SEQ ID NO: 2) in the case of Tyr589 and CSDNEYFY*VDFREY (SEQ ID NO: 3) in the case of Tyr591 (where Y*=phosphotyrosine) are described in the Examples, below. It will be appreciated by those of skill in the art that longer or shorter phosphopeptide antigens may be employed. See Id. A peptide antigen comprising both phospho-Tyr589 and phospho-Tyr591 may alternatively be employed to generate a Flt3 antibody that binds Flt3 only when phosphorylated at both positions. Polyclonal Flt3 antibodies produced as described herein may be screened as further described below.

Monoclonal antibodies of the invention may be produced in a hybridoma cell line according to the well-known technique of Kohler and Milstein. *Nature* 265: 495–97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275–81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.*, 82: 8653 (1985); Spira et al., *J. Immunol. Methods*, 74: 307 (1984)).

The invention also provides hybridoma clones, constructed as described above, that produce Flt3 monoclonal antibodies of the invention. In a preferred embodiment, the Flt3(Tyr591) monoclonal antibody of the invention is monoclonal antibody CST #25-54 produced by clone 25-54. Similarly, the invention includes recombinant cells producing a Flt3 antibody as disclosed herein, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

The hybridoma cell line 25-54, which produces monoclonal antibody CST #25-54 (54H1) that binds Flt3 when phosphorylated at tyrosine 591 (Tyr591), was deposited with the American Type Culture Collection, in accordance with the provisions of the Budapest Treaty on Feb. 21, 2002, and has been assigned ATCC Accession Number PTA-4089. The address of the ATCC is: American Type Culture Collection, 10801 University Boulevard, Manassas, Va. 20110-2209.

Flt3 antibodies of the invention, whether polyclonal or monoclonal, may be screened for epitope and phospho-specificity according to standard techniques. See, e.g. Czernik et al., *Methods in Enzymology*, 201: 264–283 (1991). For example, the antibodies may be screened against the phospho and non-phospho peptide library by ELISA to ensure specificity for both the desired antigen (i.e. that epitope including Tyr589 or Tyr591, respectively) and for reactivity only with the phosphorylated form of the antigen. Peptide competition assays may be carried out to confirm lack of reactivity with other Flt3 phosphoepitopes. The antibodies may also be tested by Western blotting against cell preparations containing Flt3, e.g. cell lines over-expressing Flt3, to confirm reactivity with the desired phosphorylated target. Specificity against the desired phosphorylated epitopes may also be examined by construction Flt3 mutants lacking phosphorylatable residues at positions outside the desired epitope known to be phosphorylated, or by mutating the desired phospho-epitope and confirming lack of reactivity. Flt3 antibodies of the invention may exhibit some cross-reactivity with non-Flt3 epitopes. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-Flt3 proteins is readily characterized by Western blotting alongside markers of known molecular weight. Amino acid sequences of cross-reacting proteins may be examined to identify sites highly homologous to the Flt-3 sequence surrounding Tyr589 and Tyr591.

In certain cases, polyclonal antisera may be exhibit some undesirable general cross-reactivity to phosphotyrosine, which may be removed by further purification of antisera, e.g. over a phosphotyramine column.

Flt-3 antibodies may be further characterized via immunohistochemical (IHC) staining using normal and diseased tissues to examine Flt-3 phosphorylation and activation status in diseased tissue. IHC may be carried out according to well known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

B. Detection & Profiling Methods

The methods disclosed herein may be employed with any biological sample suspected of containing phosphorylated Flt3. Biological samples taken from human subjects for use in the methods disclosed herein are generally biological fluids such as serum, blood plasma, fine needle aspirate, ductal lavage, bone marrow sample or ascites fluid. In the alternative, the sample taken from the subject can be a tissue sample (e.g., a biopsy tissue), such as tumor tissue.

In one embodiment, the invention provides a method for detecting phosphorylated Flt3 in a biological sample by (a) contacting (binding) a biological sample suspected of containing phosphorylated Flt3 with at least one detectable reagent that binds to Flt3 when phosphorylated at Tyr589 or Tyr591 in the intracellular domain under conditions suitable for formation of a reagent-Flt3 complex, and (b) detecting the presence of the complex in the sample, wherein the presence of the complex indicates the presence of phosphorylated Flt3(Tyr589 or Tyr591) in the sample. In a preferred embodiment, the reagent is a Flt3 antibody of the invention. Biological samples may be obtained from subjects suspected of having a disease involving altered Flt3 expression or activity (e.g., leukemia or myelodysplastic syndromes), particularly cancer and AML. Samples may be analyzed to monitor subjects who have been previously diagnosed as having cancer, to screen subjects who have not been previously diagnosed as carrying cancer, or to monitor the desirability or efficacy of therapeutics targeted at Flt3. In the case of AML, for example, the subjects will most frequently be adult males and females.

In another embodiment, the invention provides a method for profiling Flt3 activation in a test tissue suspected of involving altered Flt3 activity, by (a) contacting the test tissue with at least one detectable reagent that binds to Flt3 when phosphorylated at Tyr589 or Tyr591 in the intracellular domain under conditions suitable for formation of a reagent-Flt3 complex, (b) detecting the presence of the complex in the test tissue, wherein the presence of the complex indicates the presence of phosphorylated Flt3 (Tyr589 or Tyr591) in the test tissue, and (c) comparing the presence of phosphorylated Flt3 detected in step (b) with the presence of phosphorylated Flt3 in a control tissue, wherein a difference in Flt3 phosphorylation profiles between the test and control tissues indicates altered Flt3 activation in the test tissue. In a preferred embodiment, the reagent is a Flt3 antibody of the invention. In other preferred embodiments, the test tissue is a cancer tissue, such as an AML tissue, suspected of involving altered Flt3 Tyr589 and/or Tyr591 phosphorylation.

The methods described above are applicable to examining tissues or samples from Flt3 related cancers, particularly AML, in which phosphorylation of Flt3 at Tyr589 and/or Tyr591 has predictive value as to the outcome of the disease or the response of the disease to therapy. It is anticipated that the Flt3 antibodies will have diagnostic utility in a disease characterized by, or involving, altered Flt-3 activity or altered Flt-3 Tyr589 and/or Tyr591 phosphorylation. The methods are applicable, for example, where samples are taken from a subject has not been previously diagnosed as having AML, nor has yet undergone treatment for AML, and the method is employed to help diagnose the disease, monitor the possible progression of the cancer, or assess risk of the subject developing such cancer involving Flt3(Tyr589 or Tyr591) phosphorylation. Such diagnostic assay may be carried out prior to preliminary blood evaluation or surgical surveillance procedures.

Such a diagnostic assay may be employed to identify patients with activated Flt3 who would be most likely to respond to cancer therapeutics targeted at inhibiting Flt3 activity. Such a selection of patients would be useful in the clinical evaluation of efficacy of existing or future Flt3 inhibitors, as well as in the future prescription of such drugs to patients. Accordingly, in another embodiment, the invention provides a method for selecting a patient suitable for Flt3 inhibitor therapy, said method comprising the steps of (a) obtaining at least one biological sample from a patient that is a candidate for Flt3 inhibitor therapy, (b) contacting the biological sample with at least one detectable reagent that binds to Flt3 when phosphorylated at Tyr589 or Tyr591 in the intracellular domain (SEQ ID NO: 1) under conditions suitable for formation of a reagent-Flt3 complex, and (c) detecting the presence of the complex in the biological sample, wherein the presence of said complex indicates the presence of phosphorylated Flt3(Tyr589 or Tyr591) in said test tissue, thereby identifying the patient as suitable for Flt3 inhibitor therapy. In a preferred embodiment, the detectable reagent comprises a phospho-Flt3 antibody of the invention.

Alternatively, the methods are applicable where a subject has been previously diagnosed as having AML, and possibly has already undergone treatment for the disease, and the method is employed to monitor the progression of such cancer involving Flt3(Tyr589 or Tyr591) phosphorylation, or the treatment thereof.

In another embodiment, the invention provides a method for identifying a compound which modulates phosphorylation of Flt3 in a test tissue, by (a) contacting the test tissue with the compound, (b) detecting the level of phosphorylated Flt3 in said test tissue of step (a) using at least one detectable reagent that binds to Flt3 when phosphorylated at Tyr589 or Tyr591 in the intracellular domain under conditions suitable for formation of a reagent-Flt3 complex, and (c) comparing the level of phosphorylated Flt3 detected in step (b) with the presence of phosphorylated Flt3 in a control tissue not contacted with the compound, wherein a difference in Flt3 phosphorylation levels between the test and control tissues identifies the compound as a modulator of Flt3 phosphorylation. In a preferred embodiment, the reagent is a Flt3 antibody of the invention. In other preferred embodiments, the test tissue is a taken from a subject suspected of having cancer and the compound is a Flt3 inhibitor. The compound may modulate Flt3 activity either positively or negatively, for example by increasing or decreasing phosphorylation or expression of Flt3. Flt3 phosphorylation and activity may be monitored, for example, to determine the efficacy of an anti-Flt3 therapeutic, e.g. a Flt3 inhibitor.

Conditions suitable for the formation of antibody-antigen complexes or reagent-Flt3 complexes are well known in the art (see part (d) below and references cited therein). It will be understood that more than one Flt3 antibody may be used in the practice of the above-described methods. For example, a phospho-Flt3(Tyr589) antibody and a phospho-Flt3(Tyr591) antibody may be simultaneously employed to detect phosphorylation of both tyrosines in one step.

C. Immunoassay Formats & Diagnostic Kits

Assays carried out in accordance with methods of the present invention may be homogeneous assays or heterogeneous assays. In a homogeneous assay the immunological reaction usually involves a Flt3-specific reagent (e.g. a Flt3 antibody of the invention), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radioisotopes, fluorescent dyes, enzymes, bacteriophages, coenzymes, and so forth.

In a heterogeneous assay approach, the reagents are usually the specimen, a Flt3-specific reagent (e.g., the Flt3 antibody of the invention), and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof which may be useful for carrying out the methods disclosed herein are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well described. See id. Monoclonal antibodies of the invention may be used in a "two-site" or "sandwich" assay, with a single cell line serving as a source for both the labeled monoclonal antibody and the bound monoclonal antibody. Such assays are described in U.S. Pat. No. 4,376,110. The concentration of detectable reagent should be sufficient such that the binding of phosphorylated Flt3 is detectable compared to background.

Flt3 antibodies disclosed herein may be conjugated to a solid support suitable for a diagnostic assay (e.g., beads, plates, slides or wells formed from materials such as latex or polystyrene) in accordance with known techniques, such as precipitation. Antibodies of the invention, or other Flt3 binding reagents, may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Flt3 antibodies of the invention may also be optimized for use in a flow cytometry assay to determine the activation status of Flt3 in patients before, during, and after treatment with a drug targeted at inhibiting Flt3 phosphorylation at Tyr589 or Tyr591. For example, bone marrow cells or peripheral blood cells from patients may be analyzed by flow cytometry for Flt3 phosphorylation, as well as for markers identifying various hematopoietic cell types. In this manner, Flt3 activation status of the malignant cells may be specifically characterized. Flow cytometry may be carried out according to standard methods. See, e.g. Chow et al., Cytometry (Communications in Clinical Cytometry) 46: 72–78 (2001). Briefly and by way of example, the following protocol for cytometric analysis may be employed: fixation of the cells with 1% paraformaldehyde for 10 minutes at 37° C. followed by permeabilization in 90% methanol for 30 minutes on ice. Cells may then be stained with the primary Flt3 antibody, washed and labeled with a fluorescent-labeled secondary antibody. Alternatively, the cells may be stained with a fluorescent-labeled primary antibody. The cells would then be analyzed on a flow cytometer (e.g. a Beckman Coulter EPICS-XL) according to the specific protocols of the instrument used. Such an analysis would identify the presence of activated Flt3 in the malignant cells and reveal the drug response on the targeted Flt3 protein.

Alternatively, Flt3 antibodies of the invention may be optimized for use in other clinically-suitable applications, for example bead-based multiplex-type assays, such as IGEN, Luminex™ and/or Bioplex™ assay formats, or otherwise optimized for antibody arrays formats.

Diagnostic kits for carrying out the methods disclosed above are also provided by the invention. Such kits comprise at least one detectable reagent that binds to Flt3 when phosphorylated at Tyr589 or Tyr591 in the intracellular domain. In a preferred embodiment, the reagent is a Flt3 antibody of the invention. In one embodiment, the diagnostic kit comprises (a) a Flt3 antibody of the invention (i.e. a phospho-specific antibody that binds phospho-Flt3(Tyr589)

or phospho-Flt3(Tyr591)) conjugated to a solid support and (b) a second antibody conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. In another embodiment a kit (e.g. a kit for the selection of a patient suitable for Flt3 inhibitor therapy) comprises (a) a Flt3 antibody as described herein, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

The following Examples are provided only to further illustrate the invention, and are not intended to limit its scope, except as provided in the claims appended hereto. The present invention encompasses modifications and variations of the methods taught herein which would be obvious to one of ordinary skill in the art.

EXAMPLE 1

Production of a Flt3(Tyr589) Phosphospecific Polyclonal Antibody

A previously unknown Flt3 phosphorylation site, tyrosine 589, was discovered as described above by amino acid comparison to the Eph RTK family juxta-transmembrane domain, and confirmation as a putative kinase phosphorylation site using the ScanSite program. See Ybenga-Groot et al., supra.; Yaffe et al., supra. An 11 amino acid phospho-peptide antigen, CSDNEY*FYDVF (SEQ ID NO: 2) (where Y*=phosphotyrosine), corresponding to residues 585–594 of human Flt-3 (SEQ ID NO: 1) plus cysteine on the C-terminal for coupling, was constructed according to standard synthesis techniques using a Rainin/Protein Technologies, Inc., Symphony peptide synthesizer. See ANTIBODIES: A LABORATORY MANUAL, supra.; Merrifield, supra.

This peptide was coupled to KLH, and rabbits were injected intradermally (ID) on the back with antigen in complete Freunds adjuvant (500 µg antigen per rabbit). The rabbits were boosted with same antigen in incomplete Freund adjuvant (250 µg antigen per rabbit) every three weeks. After the fifth boost, the bleeds were collected. The sera were purified by Protein A-affinity chromatography as previously described (see ANTIBODIES: A LABORATORY MANUAL, Cold Spring Harbor, supra.). The eluted immunoglobulins were further loaded onto CSDNEYFYDVF-resin Knotes column. The flow through fraction was collected and applied onto CSDNEY*FYDVF-resin column. After washing the column extensively, the phospho-FLT3 (Tyr589) antibodies were eluted and kept in antibody storage buffer.

Figure 2A:
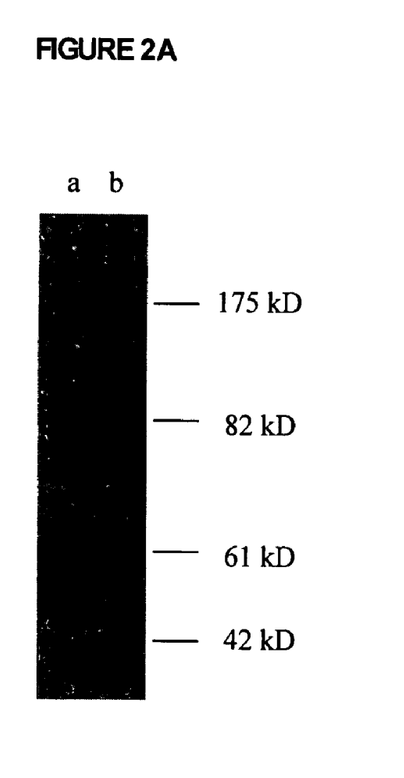
FIG. 2A—is a Western blot analysis using phospho-Flt3 (Tyr589) polyclonal antibody on extracts of Baf3 cells transfected with Flt-3 either not stimulated (lane a) or stimulated with Flt3 ligand (lane b).

The antibody was tested for phosphospecificity using Western blot assay. BaF3/FLT3 cells were obtained from Hutchison Cancer Research Center in Seattle, Wash. BaF3/FLT3 cells were cultured in DMEM supplemented with 10% FCS and 5 U/ml IL-3. Before stimulation, the cells were starved in serum-free DMEM medium for 4 hours. The cells were stimulated with FLT3 ligand (50 ng/ml) for 5 minutes. The cells were collected, washed with PBS and directly lysed in cell lysis buffer. The protein concentration of cell lysates were measured. The loading buffer was added into cell lysate and the mixture was boiled at 100° C. for 5 minutes. 20 µl (10 µg protein) of sample was added onto 7.5% SDS-PAGE gel. A standard Western blot was performed according to the Immunoblotting Protocol set out in the Cell Signaling Technology 2002 Catalogue and Technical Reference, p. 282. The phospho-FLT3 (Tyr589) polyclonal antibody was used at dilution 1:1000. The results of the blots are shown in FIG. 2A. As shown in the Figure, the antibody, as expected, only recognizes the ~140 kDa FLT3 activated by its ligand. It does not recognize the non-tyrosine phosphorylated FLT3 in the non-stimulated cells.

Figure 2B:
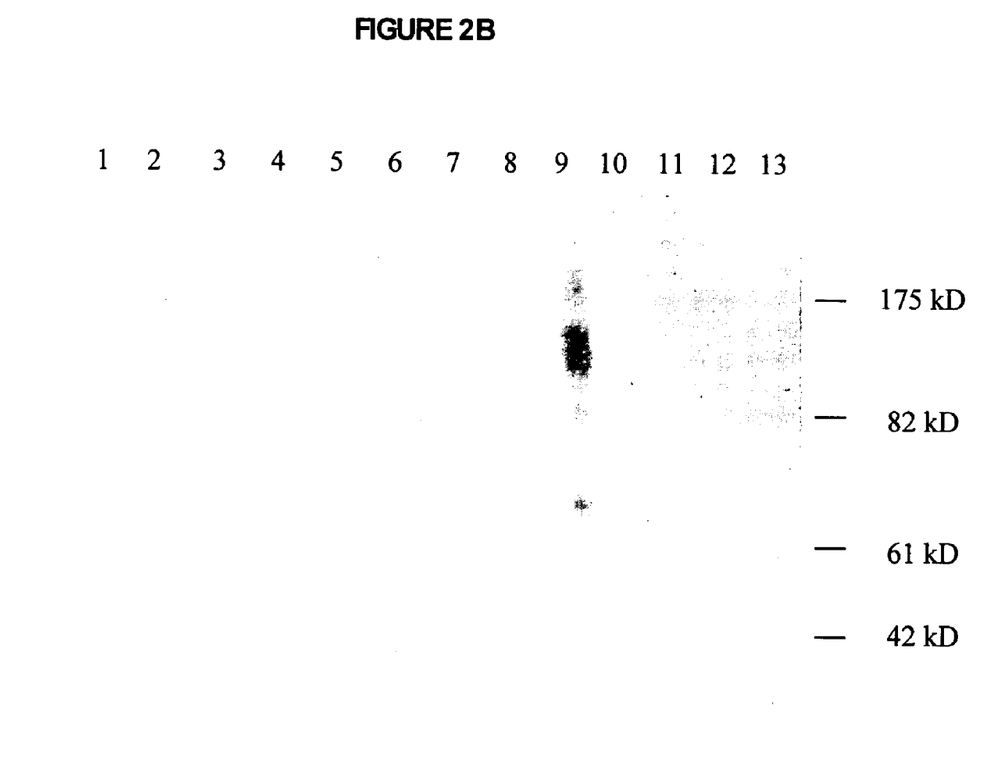
FIG. 2B—is a Western blot analysis using phospho-Flt3 (Tyr589) polyclonal antibody on various stimulated and unstimulated cell extracts expressing various RTKs. Lane 1: A431 cell: no-stimulation; Lane 2: A431 cells: EGF-stimulated; Lane 3: CHO-IR/IRS-1: no-stimulation; Lane 4: CHO-IR/IRS-1: Insulin-stimulated; Lane 5: PAE/KDR: no-stimulation; Lane 6: PAE/KDR: VEGF-stimulated; Lane 7: FDCP1/fms: no-stimulation; Lane 8: FDCP1/fms: M-CSF-stimulated; Lane 9: Cos cells expressing activated FGFR1; Lane 10: K562 cells; Lane 11: NIH-3T3 cells: PDGF-stimulated; Lane 12: mlMCD-3 cells: no-stimulation; Lane 13: mlMCD-3 cells: HGF-stimulated.

In order to confirm the specificity, different cell lysates containing various tyrosine-phosphorylated RTKs were prepared. The Western blot assay was performed using these cell lysates. The phospho-FLT3 (Tyr589) polyclonal antibody was used (1:1000 dilution) to react with the different phospho-RTKs on Western blot membrane. The results are shown in FIG. 2B. The antibody does not significantly cross-react with other highly tyrosine-phosphorylated RTKs, with exception of slight binding with FGFR1.

EXAMPLE 2

Production of a Flt3(Tyr591) Phosphospecific Polyclonal Antibody

A second previously unknown Flt3 phosphorylation site, tyrosine 591, was discovered as described in Example 1, above, by protein sequence comparison to the Eph juxta-transmembrane domain. A 14 amino acid phospho-peptide antigen, CSDNEYFY*DVFREY (SEQ ID NO: 3) (where Y*=phosphotyrosine), corresponding to residues 585–597 of human Flt-3 (SEQ ID NO: 1) plus cysteine on the C-terminal for coupling, was constructed according to standard synthesis techniques using a Rainin/Protein Technologies, Inc., Symphony peptide synthesizer. See ANTIBODIES: A LABORATORY MANUAL, supra.; Merrifield, supra.

This peptide was coupled to KLH, and used to immunize rabbits, and purified over protein A as described in Example 1. Antibody having the desired specificity was purified by peptide-affinity chromatography using the DNEYFY*VDFREY peptide.

Figure 3A:
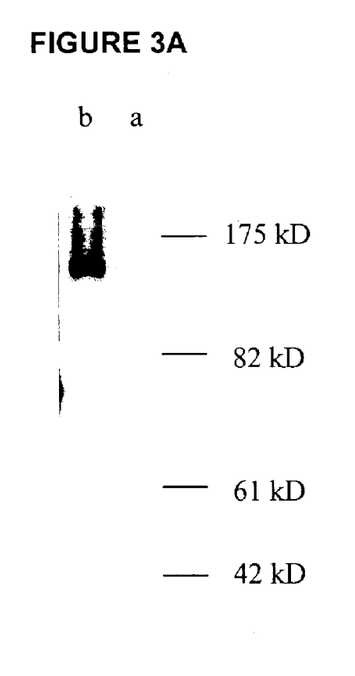
FIG. 3A—is a Western blot analysis using phospho-Flt3 (Tyr591) polyclonal antibody on extracts of Baf3 cells transfected with Flt-3 either not stimulated (lane a) or stimulated with Flt3 ligand (lane b).
Figure 3B:
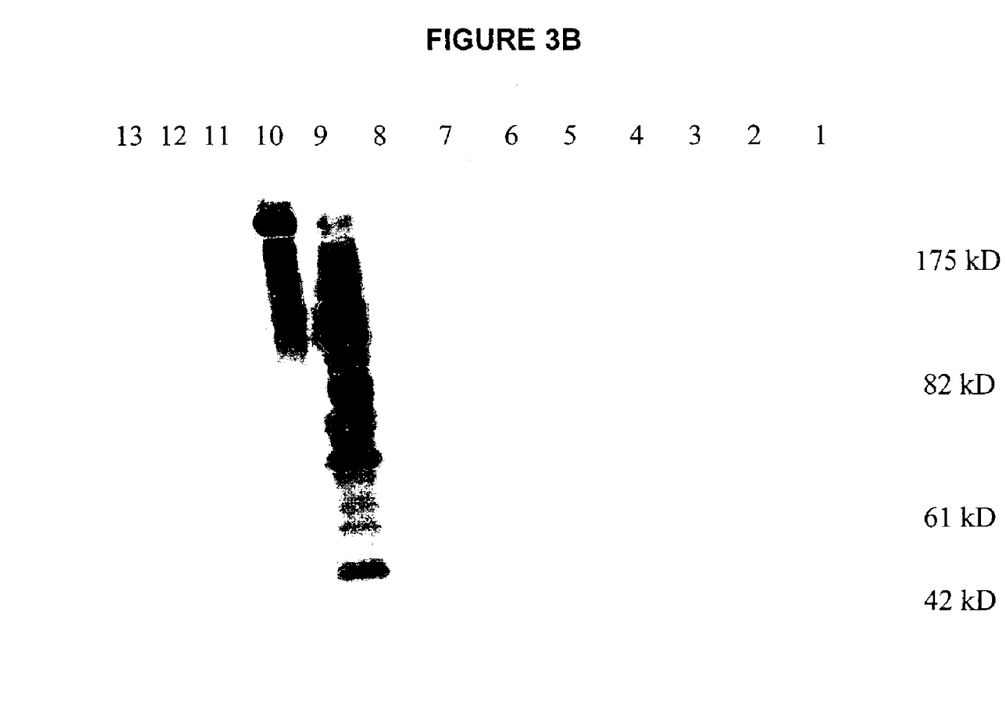
FIG. 3B—is a Western blot analysis using phospho-Flt3 (Tyr591) polyclonal antibody on various stimulated and unstimulated cell extracts expressing various RTKs. Lane 1: A431 cell: no-stimulation; Lane 2: A431 cells: EGF-stimulated; Lane 3: CHO-IR/IRS-1: no-stimulation; Lane 4: CHO-IR/IRS-1: Insulin-stimulated; Lane 5: PAE/KDR: no-stimulation; Lane 6: PAE/KDR: VEGF-stimulated; Lane 7: FDCP1/fms: no-stimulation; Lane 8: FDCP1/fms: M-CSF-stimulated; Lane 9: Cos cells expressing activated FGFR1; Lane 10: K562 cells Lane 11: NIH-3T3 cells: PDGF-stimulated; Lane 12: mlMCD-3 cells: no-stimulation Lane 13: mlMCD-3 cells: HGF-stimulated.

The phospho-Flt3(Tyr591) antibody was tested for phosphospecificity using Western blot assay as described in Example 1 above. The results with Baf3 cell are shown in FIG. 3A and with various extracts expressing different RTKs in FIG. 3B. As expected, this antibody only recognizes the ~140 kDa FLT3 activated by its ligand. It does not recognize the non-tyrosine phosphorylated FLT3 in the non-stimulated cells. Moreover, the antibody does not significantly cross-react with other highly tyrosine-phosphorylated RTKs, with the exception of Bcr-Abl and FGFR1.

EXAMPLE 3

Production of a Flt3(Tyr591) Phosphospecific Monoclonal Antibody

A Flt3(Tyr591) phosphospecific monoclonal antibody, CST #25-54, was produced from spleen cells of the immunized BALB/c mouse described in Example 2, above, following standard procedures (Harlow and Lane, 1988). The mouse was fused to SP2/0 mouse myeloma fusion partner cells according to the protocol of Kohler and Milstein (1975). Colonies originating from the fusion were screened by ELISA for reactivity to the phospho-peptide and non-phospho-peptide and by Western blot analysis. Colonies found to be positive by ELISA to the phospho-peptide while negative to the non-phospho-peptide were further characterized by Western blot analysis. Colonies found to be positive by Western blot analysis were subcloned by limited dilution. Mouse ascites were produced from the single clone obtained from subcloning. From the original fusion, 26 clones were found to be phospho-specific on ELISA. Only one of these clones was positive on Western blot analysis using cell culture supernatant, showing phospho-specificity as indicated by a strong band in the induced lane and a weak band in the uninduced lane. This clone was subcloned to produce the #25-54 clone.

Figure 4:
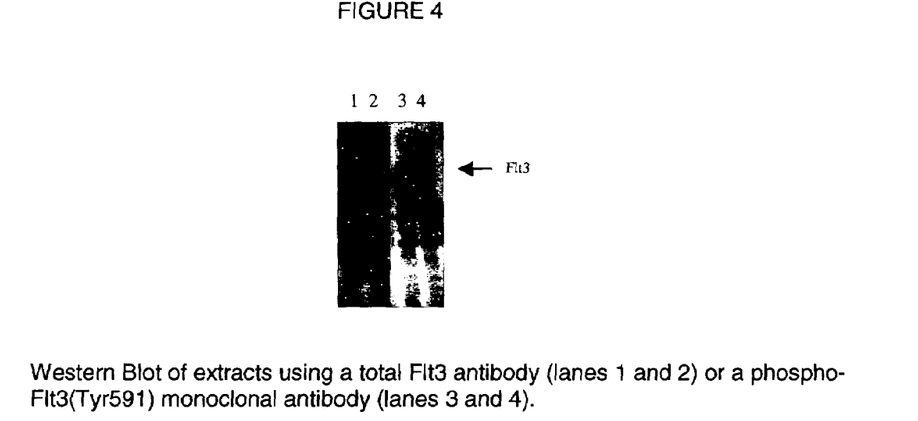

Ascites fluid from the single clone obtained from the Flt3 fusion was further tested by Western blot analysis. The ascites fluid gave similar results on Western blot analysis as observed previously with the cell culture supernatant, indicating phospho-specificity on Flt3 ligand-induced Baf3 cells (FIG. 4; lane 3 versus lane 4).

EXAMPLE 4

Detection of Flt3 Phosphorylation in Cytometric Assay

The Flt3(Tyr591) phosphospecific polyclonal antibody described in Example 2 was used in flow cytometry to detect phospho-Flt3(Tyr591) in Flt3 ligand induced Baf3 murine hematopoietic cell line. Baf3 cells that had been transfected with a Flt3 construct were serum starved for 4 hours, treated with 4 ug/ml Flt3 ligand for 5 minutes at 37° C. A sample of the cells was taken to be analyzed by Western blot analysis. The remaining cells were fixed with 1% paraformaldehyde for 10 minutes at 37° C., followed by cell permeabilization 90% with methanol for 30 minutes on ice. The fixed cells were then stained with the Flt3(Tyr591) primary antibody for 60 minutes at room temperature. The cells were then washed and stained with an Alexa 488-labeled secondary antibody for 30 minutes at room temperature. The cells were then analyzed on a Beckman Coulter EPICS-XL flow cytometer.

Figure 5:
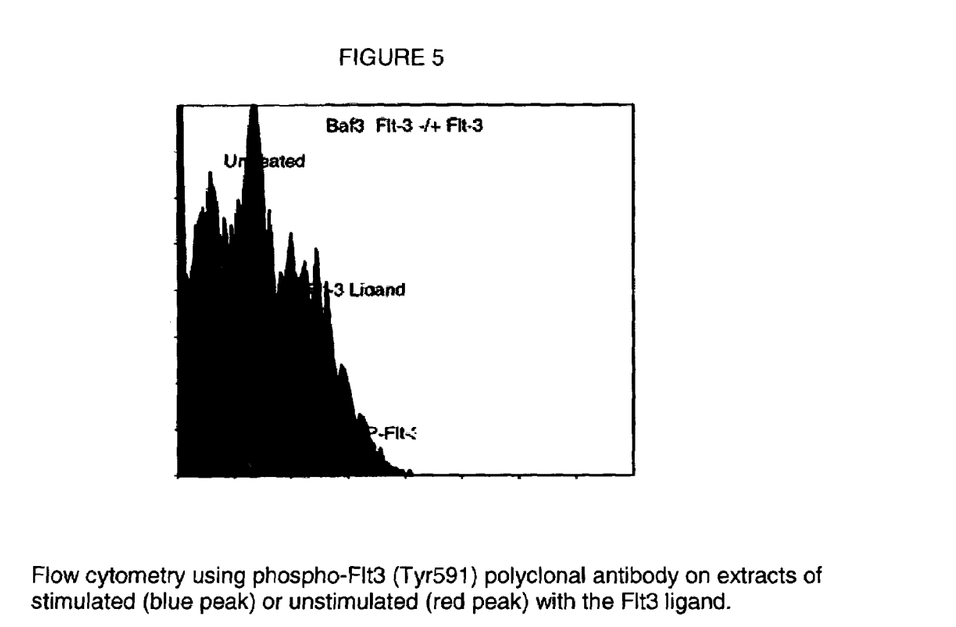
FIG. 5—is a flow cytometric graph of Flt3 activation in Baf3 cells transfected with Flt3 and stimulated with Flt3 ligand, detected using a polyclonal phospho-Flt3(Tyr591) antibody.

The cytometric results matched the Western results described above, further demonstrating the specificity of the Flt3(Tyr591) polyclonal antibody for the activated Flt3 protein (FIG. 5; induced (blue) peak versus un-induced (red) or secondary control (green and purple) peaks).

EXAMPLE 5

Detection of Constitutively Active Flt3 in Cells using Flow Cytometry

Flt3(Tyr591) phosphospecific monoclonal antibody CST #25-54 was used in flow cytometry to detect phospho-Flt3 (Tyr591) in the EOL-1 hematopoietic cell line that expresses an endogenous, constitutively active Flt3. Serum-starved cells were incubated with or without the small molecule Flt3 inhibitor AG1296 for 4 hours at 37° C. The cells then were fixed with 2% paraformaldehyde for 10 minutes at 37° C. followed by cell permeabilization 90% with methanol for 30 minutes on ice. The fixed cells were then stained with the Alexa 488-conjugated Flt3 primary antibody for 1 hour at room temperature. The cells were then analyzed on a Beckman Coulter EPICS-XL flow cytometer.

Figure 6:
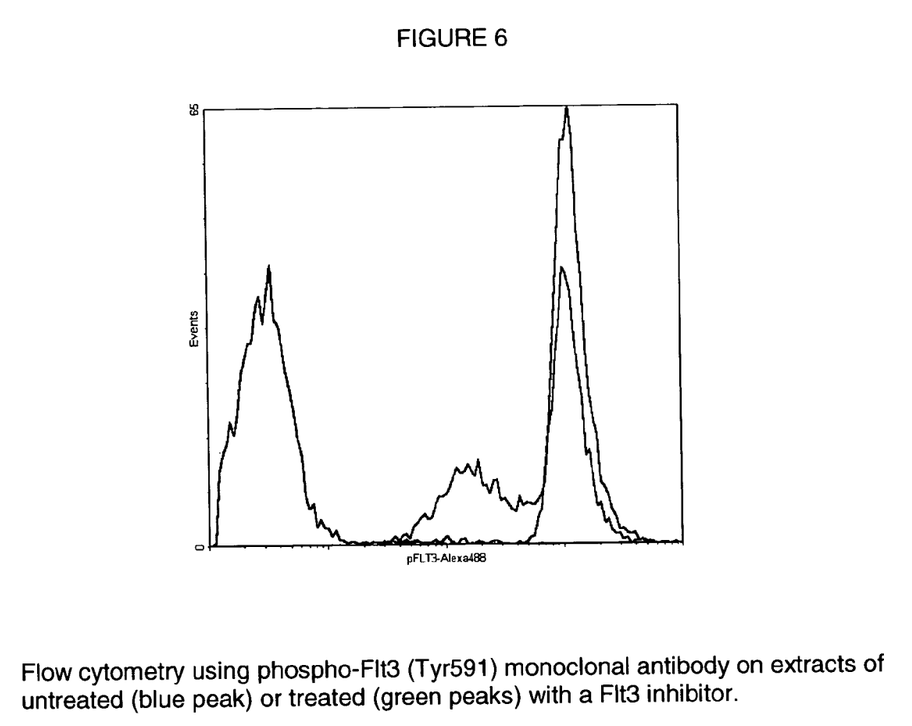
FIG. 6—is a flow cytometric graph of Flt3 activation in EOL-1 cells expressing constitutively activated Flt3 with and without a Flt3 inhibitor (AG1296), detected using a monoclonal phospho-Flt3(Tyr591) antibody.

The cytometric results demonstrate the specificity of the Flt3(Tyr591) monoclonal antibody for the activated Flt3 protein and the assay's ability to detect the activity and efficacy of a Flt3 inhibitor (FIG. 6). In the presence of the drug, a population of the cells show less staining with the antibody (left green peak; approximately 30% of the total cells), indicating that the drug is active against Flt3.

---

What is claimed is:

1. An isolated antibody that specifically binds to FMS-related tyrosine kinase 3 (Flt3) only when phosphorylated at tyrosine 589 (SEQ ID NO: 1) in the intracellular domain, but does not bind Flt3 when not phosphorylated at this position nor to other phosphorylated tyrosine residues in Flt3.

2. An isolated antibody that specifically binds to Flt3 only when phosphorylated at tyrosine 591 (SEQ ID NO: 1) in the intracellular domain, but does not bind Flt3 when not phosphorylated at this position nor to other phosphorylated tyrosine residues in Flt3.

3. The antibody of claim 1 or 2, wherein said antibody is polyclonal.

4. The antibody of claim 1 or 2, wherein said antibody is monoclonal.

5. A hybxrdoma cell line producing the antibody of claim 4.

6. The hybridoma cell line of claim 5, wherein said cell line is a rabbit hybridoma or a mouse hybridoma.

7. The hybridoma cell line of claim 5, wherein said cell line is ATCC Accession No. FTA-4089.

8. A monoclonal antibody (CST #25-54) produced by the hybridoma cell line of claim 7.

9. A method for detecting phosphorylated Flt3 in a biological sample, said method comprising the steps of:

(a) contacting a biological sample suspected of containing phosphorylated Flt3 with at least one detectable reagent that binds to Flt3 when phosphorylated at either Tyr589 or Tyr591 in the intracellular domain (SEQ ID NO:1), wherein said detectable reagent comprises an antibody of claim 1 or 2, under conditions suitable for formation of a reagent-Flt3 complex; and (b) detecting the presence of said complex in said sample, wherein the presence of said complex indicates the presence of phosphorylated Flt3(Tyr589 or Tyr591, respectively) in said sample.

10. The method of claim 9, wherein said biological sample is taken from a subject suspected of having cancer.

11. A method for profiling Flt3 activation in a test tissue suspected of involving altered Flt2 activity, said method comprising the steps of:

(a) contacting said test tissue with at least one detectable reagent that binds to Flt3 when phosphorylated at Tyr589 or Tyr591 in the intracellular domain (SEQ ID NO:1), wherein said detectable reagent comprises an antibody of claim 1 or 2, under conditions suitable for formulation of a reagent-Flt2 complex;

(b) detecting the presence of said complex in said test tissue, wherein the presence of said complex indicates the presence of phosphorylated Flt3(Tyr589 or Tyr591) in said test tissue; and (c) comparing the presence of phosphorylated Flt3 detected in step (b) with the presence of phosphorylated Flt3 in a control tissue, wherein a difference in Flt3 phosphorylation profiles between said test tissue and said control tissue indicates altered Flt3 activation in said test tissue.

12. The method of claim 11, wherein said test tissue is taken from a subject suspected of having cancer.

13. A method of identifying a compound which modulates phosphorylation of Flt3 in a test tissue, said method comprising the steps of:
   (a) contacting said test tissue with said compound;
   (b) detecting the level of phosphorylated Flt3 in said test tissue of step (a) using at least one detectable reagent that binds to Flt3 when phosphorylated at Tyr589 or Tyr591 in the intracellular domain (SEQ ID NO:1), wherein said at least one detectable reagent comprises an antibody of claim 1 or 2, under conditions suitable for formation of a reagent-Flt3 complex;
   (c) comparing the level of phosphorylated Flt3 detected in step (b) with the presence of phosphorylated Flt3 in a control tissue not contacted with said compound, wherein a difference in Flt3 phosphorylation levels between said test tissue and said control tissue identifies said compound as a modulator of Flt phosphorylation.

14. The method of claim 13, wherein said test tissue is taken from a subject suspected of having cancer.

15. The method of claim 13, wherein said compound is a Flt3 inhibitor.

* * * * *

SEQUENCE LISTING

<160> NUMBER OF SEQ ID NOS: 3

<210> SEQ ID NO 1
<211> LENGTH: 993
<212> TYPE: PRT
<213> ORGANISM: Homo sapiens

<400> SEQUENCE: 1

```
Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
        35                  40                  45

Lys Ser Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Arg Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
```

-continued

```
                115                 120                 125
Val Ile Leu Lys Met Thr Glu Thr Gln Ala Gly Glu Tyr Leu Leu Phe
    130                 135                 140
Ile Gln Ser Glu Ala Thr Asn Tyr Thr Ile Leu Phe Thr Val Ser Ile
145                 150                 155                 160
Arg Asn Thr Leu Leu Tyr Thr Leu Arg Arg Pro Tyr Phe Arg Lys Met
                165                 170                 175
Glu Asn Gln Asp Ala Leu Val Cys Ile Ser Glu Ser Val Pro Glu Pro
                180                 185                 190
Ile Val Glu Trp Val Leu Cys Asp Ser Gln Gly Glu Ser Cys Lys Glu
            195                 200                 205
Glu Ser Pro Ala Val Val Lys Lys Glu Glu Lys Val Leu His Glu Leu
    210                 215                 220
Phe Gly Met Asp Ile Arg Cys Cys Ala Arg Asn Glu Leu Gly Arg Glu
225                 230                 235                 240
Cys Thr Arg Leu Phe Thr Ile Asp Leu Asn Gln Thr Pro Gln Thr Thr
                245                 250                 255
Leu Pro Gln Leu Phe Leu Lys Val Gly Glu Pro Leu Trp Ile Arg Cys
            260                 265                 270
Lys Ala Val His Val Asn His Gly Phe Gly Leu Thr Trp Glu Leu Glu
            275                 280                 285
Asn Lys Ala Leu Glu Glu Gly Asn Tyr Phe Glu Met Ser Thr Tyr Ser
    290                 295                 300
Thr Asn Arg Thr Met Ile Arg Ile Leu Phe Ala Phe Val Ser Ser Val
305                 310                 315                 320
Ala Arg Asn Asp Thr Gly Tyr Tyr Thr Cys Ser Ser Ser Lys His Pro
                325                 330                 335
Ser Gln Ser Ala Leu Val Thr Ile Val Glu Lys Gly Phe Ile Asn Ala
                340                 345                 350
Thr Asn Ser Ser Glu Asp Tyr Glu Ile Asp Gln Tyr Glu Glu Phe Cys
            355                 360                 365
Phe Ser Val Arg Phe Lys Ala Tyr Pro Gln Ile Arg Cys Thr Trp Thr
    370                 375                 380
Phe Ser Arg Lys Ser Phe Pro Cys Glu Gln Lys Gly Leu Asp Asn Gly
385                 390                 395                 400
Tyr Ser Ile Ser Lys Phe Cys Asn His Lys His Gln Pro Gly Glu Tyr
                405                 410                 415
Ile Phe His Ala Glu Asn Asp Asp Ala Gln Phe Thr Lys Met Phe Thr
            420                 425                 430
Leu Asn Ile Arg Arg Lys Pro Gln Val Leu Ala Glu Ala Ser Ala Ser
            435                 440                 445
Gln Ala Ser Cys Phe Ser Asp Gly Tyr Pro Leu Pro Ser Trp Thr Trp
    450                 455                 460
Lys Lys Cys Ser Asp Lys Ser Pro Asn Cys Thr Glu Glu Ile Thr Glu
465                 470                 475                 480
Gly Val Trp Asn Arg Lys Ala Asn Arg Lys Val Phe Gly Gln Trp Val
                485                 490                 495
Ser Ser Ser Thr Leu Asn Met Ser Glu Ala Ile Lys Gly Phe Leu Val
                500                 505                 510
Lys Cys Cys Ala Tyr Asn Ser Leu Gly Thr Ser Cys Glu Thr Ile Leu
            515                 520                 525
Leu Asn Ser Pro Gly Pro Phe Pro Phe Ile Gln Asp Asn Ile Ser Phe
    530                 535                 540
```

```
Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
        595                 600                 605

Asn Leu Glu Phe Gly Lys Val Leu Gly Ser Gly Ala Phe Gly Lys Val
    610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
        675                 680                 685

Leu Ile Phe Glu Tyr Cys Cys Tyr Gly Asp Leu Leu Asn Tyr Leu Arg
    690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
        755                 760                 765

Glu Asn Gln Lys Arg Leu Glu Glu Glu Glu Asp Leu Asn Val Leu Thr
    770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
    930                 935                 940

Cys Gln Leu Ala Asp Ala Glu Glu Ala Met Tyr Gln Asn Val Asp Gly
945                 950                 955                 960
```

-continued

```
Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 2
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (6)..(6)
<223> OTHER INFORMATION: PHOSPHORYLATION; tyrosine at position 6 is
      phosphorylated

<400> SEQUENCE: 2

Cys Ser Asp Asn Glu Tyr Phe Tyr Val Asp Phe
1               5                   10

<210> SEQ ID NO 3
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylated

<400> SEQUENCE: 3

Cys Ser Asp Asn Glu Tyr Phe Tyr Val Asp Phe Arg Glu Tyr
1               5                   10
```